(12) United States Patent
Makino et al.

(10) Patent No.: US 10,195,271 B2
(45) Date of Patent: Feb. 5, 2019

(54) ANTIBODY TITER-INCREASING AGENT USING LACTIC ACID BACTERIUM

(71) Applicant: Meiji Co., Ltd., Tokyo (JP)

(72) Inventors: Seiya Makino, Odawara (JP); Jun Henmi, Odawara (JP); Hiroshi Kano, Odawara (JP); Yukio Asami, Odawara (JP); Shuji Ikegami, Odawara (JP); Hiroyuki Itou, Odawara (JP); Yoshio Suzuki, Inzai (JP); Sachio Kawai, Inzai (JP); Keisuke Sawaki, Inzai (JP); Ko Okumura, Tokyo (JP); Isao Nagaoka, Tokyo (JP); Kazuyoshi Takeda, Tokyo (JP)

(73) Assignee: Meiji Co., Ltd., Tokyo (JP)

( * ) Notice: Subject to any disclaimer, the term of this patent is extended or adjusted under 35 U.S.C. 154(b) by 0 days.

(21) Appl. No.: 14/914,382

(22) PCT Filed: Aug. 26, 2014

(86) PCT No.: PCT/JP2014/072229
§ 371 (c)(1),
(2) Date: Feb. 25, 2016

(87) PCT Pub. No.: WO2015/029967
PCT Pub. Date: Mar. 5, 2015

(65) Prior Publication Data
US 2016/0206733 A1 Jul. 21, 2016

(30) Foreign Application Priority Data
Aug. 26, 2013 (JP) .................... 2013-175048

(51) Int. Cl.
*A61K 39/02* (2006.01)
*A61K 39/39* (2006.01)
*A61K 35/747* (2015.01)
*A61K 39/00* (2006.01)

(52) U.S. Cl.
CPC ............ *A61K 39/39* (2013.01); *A61K 35/747* (2013.01); *A61K 2039/55594* (2013.01)

(58) Field of Classification Search
None
See application file for complete search history.

(56) References Cited

U.S. PATENT DOCUMENTS

| 2010/0129334 A1 | 5/2010 | Samson-Villeger et al. |
| 2011/0274722 A1 | 11/2011 | Gorbach et al. |

FOREIGN PATENT DOCUMENTS

| EP | 2627198 A1 | 8/2013 |
| JP | H04-235921 A | 8/1992 |
| JP | 2001039423 A * | 5/2007 |
| JP | 2008-529535 | 8/2008 |
| JP | 5177728 | 4/2013 |
| WO | WO 2011/065300 | 6/2011 |
| WO | WO 2012/014978 | 2/2012 |
| WO | WO 2012/049301 A1 | 4/2012 |

OTHER PUBLICATIONS

De Simone et al (Nutrition Reports International (1986), 33(3), 419-33), Abstract Only.*
Racedo et al (Food and Agricultural Immunology (2009), 20(3), 231-244).*
Medici (Journal of Dairy Research (2005), 72(2), 243-249).*
Extended European Search Report for EP 14839476.0 dated Dec. 19, 2016.
Makino et al., Reducing the risk of infection in the elderly by dietary intake of yoghurt fermented with Lactobacillus delbrueckii ssp. bulgaricus OLL1073R-1. Br J Nutr. Oct. 2010;104(7):998-1006. doi: 10.1017/S000711451000173X. Epub May 21, 2010.
Boge et al., A probiotic fermented dairy drink improves antibody response to influenza vaccination in the elderly in two randomised controlled trials. Vaccine. Sep. 18, 2009;27(41):5677-84. doi: 10.1016/j.vaccine.2009.06.094. Epub Jul. 16, 2009.
Nagai et al., Effects of oral administration of yogurt fermented with Lactobacillus delbrueckii ssp. bulgaric OLL1073R-1 and its exopolysaccharides against influenza virus infection in mice. Int Immunopharmacol. Dec. 2011;11(12):2246-50. doi: 10.1016/j.intimp.2011.09.012. Epub Oct 8, 2011.
Olivares et al., Oral intake of Lactobacillus fermentum CECT5716 enhances the effects of influenza vaccination. Nutrition. Mar. 2007;23(3):254-60.
Rautio et al., Liver abscess due to a Lactobacillus rhamnosus strain indistinguishable from L. rhamnosus strain GG. Clin Infect Dis. May 1999;28(5):1159-60.
Rizzardini et al., Evaluation of the immune benefits of two probiotic strains Bifidobacterium animalis ssp. lactis, BB-12® and Lactobacillus paracasei ssp. paracasei, L. casei 431® in an influenza vaccination model: a randomised, double-blind, placebo-controlled study. Br J Nutr. Mar. 2012;107(6):876-84. doi:10.1017/S000711451100420X. Epub Sep. 7, 2011.
Salminen et al., Lactobacillus bacteremia, clinical significance, and patient outcome, with special focus on probiotic L. rhamnosus GG. Clin Infect Dis. Jan. 1, 2004;38(1):62-9. Epub Dec. 4, 2003.
Nagafuchi et al., Strain dependency of the immunopotentiating activity of Lactobacillus delbrueckii subsp. bulgaricus. Biosci Biotechnol Biochem. Mar. 1999;63(3):474-9.
Portier et al., Fermented milks and increased antibody responses against cholera in mice. Int J Immunotherapy. 1993; 9(4): 217-224.

* cited by examiner

*Primary Examiner* — Jennifer E Graser
(74) *Attorney, Agent, or Firm* — Wolf, Greenfield & Sacks, P.C.

(57) ABSTRACT

The present invention addresses the problem of providing an antibody titer-increasing agent, such as an adjuvant, capable of sustaining an effect achieved by, for example, vaccination, which is an antibody titer-increasing agent such as an adjuvant that is safe, convenient and economical and can be easily taken irrespective of age, and a method for manufacturing the same. A method for increasing an antibody titer and a method for enhancing the effect of a vaccine, each method comprising using Lactobacillus delbrueckii subspecies bulgaricus OLL1073R-1 or a culture thereof; and an antibody titer-increasing agent such as an adjuvant that comprises Lactobacillus delbrueckii subspecies bulgaricus OLL1073R-1 or a culture thereof.

11 Claims, 9 Drawing Sheets

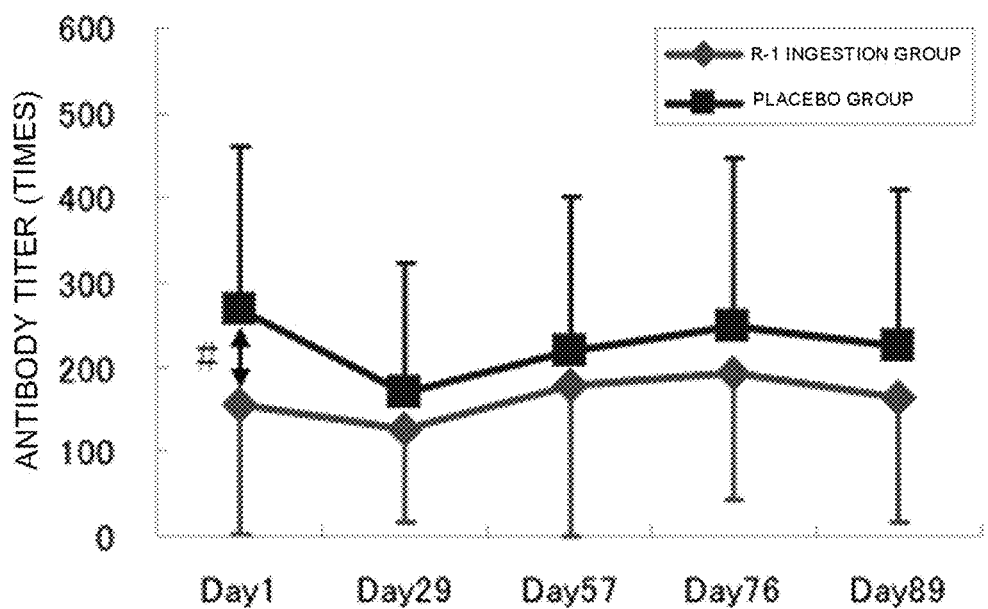
FIG. 1-1 CHANGE IN INFLUENZA A VIRUS H1N1 ANTIBODY TITER
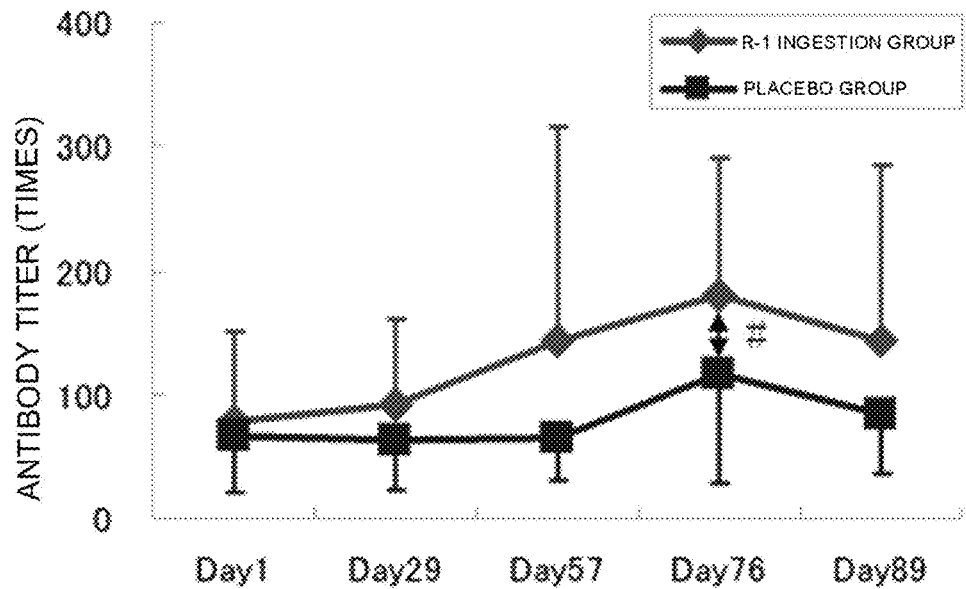
FIG. 1-2 CHANGE IN INFLUENZA A VIRUS H3N2 ANTIBODY TITER

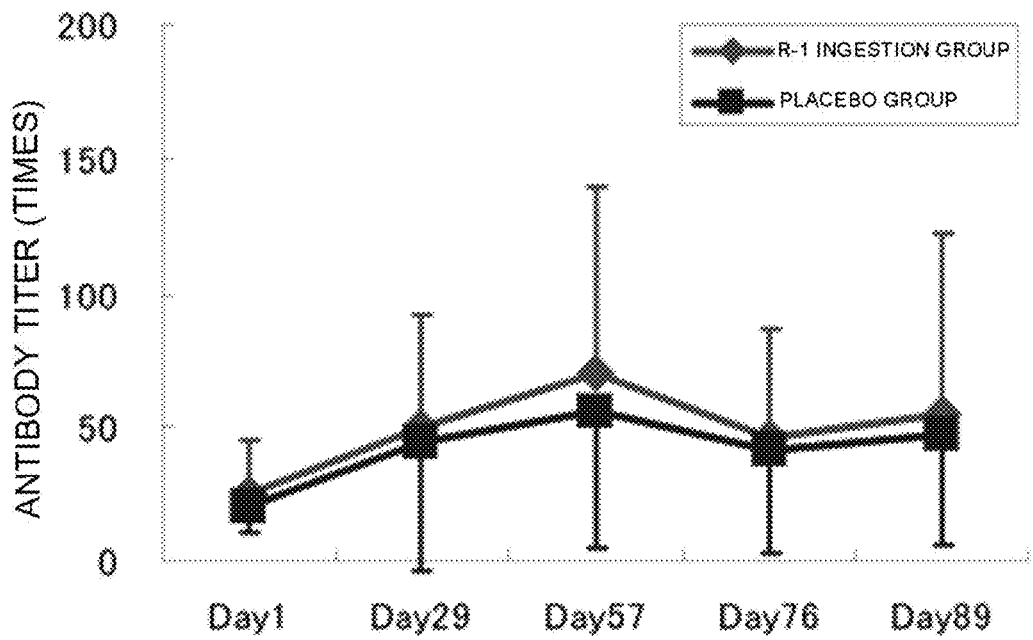
FIG. 1-3 CHANGE IN INFLUENZA B VIRUS ANTIBODY TITER
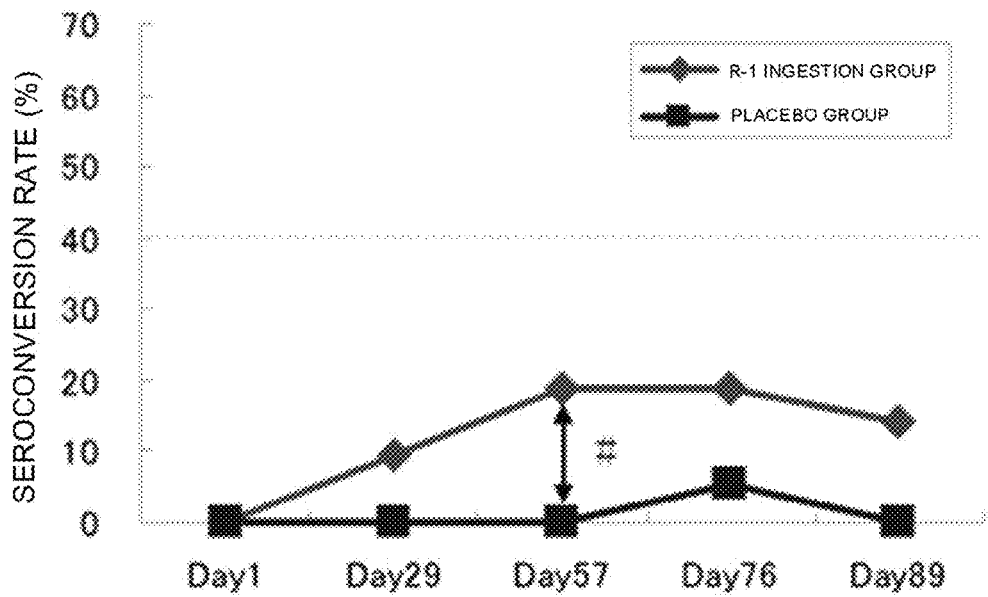
FIG. 2-1 CHANGE IN INFLUENZA A VIRUS H1N1 ANTIBODY SEROCONVERSION RATE

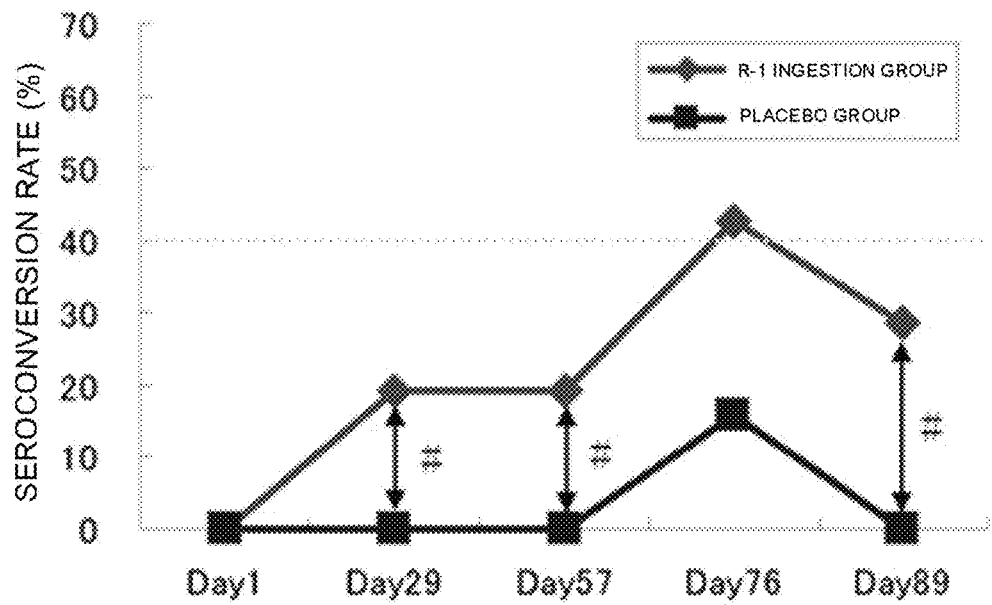
FIG. 2-2 CHANGE IN INFLUENZA A VIRUS H3N2 ANTIBODY SEROCONVERSION RATE
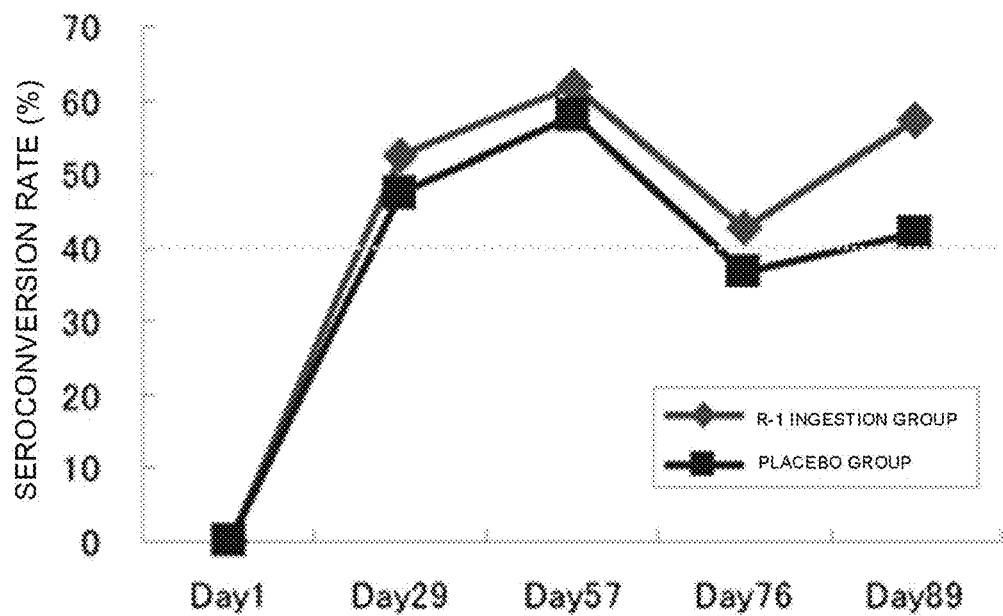
FIG. 2-3 CHANGE IN INFLUENZA B VIRUS ANTIBODY SEROCONVERSION RATE

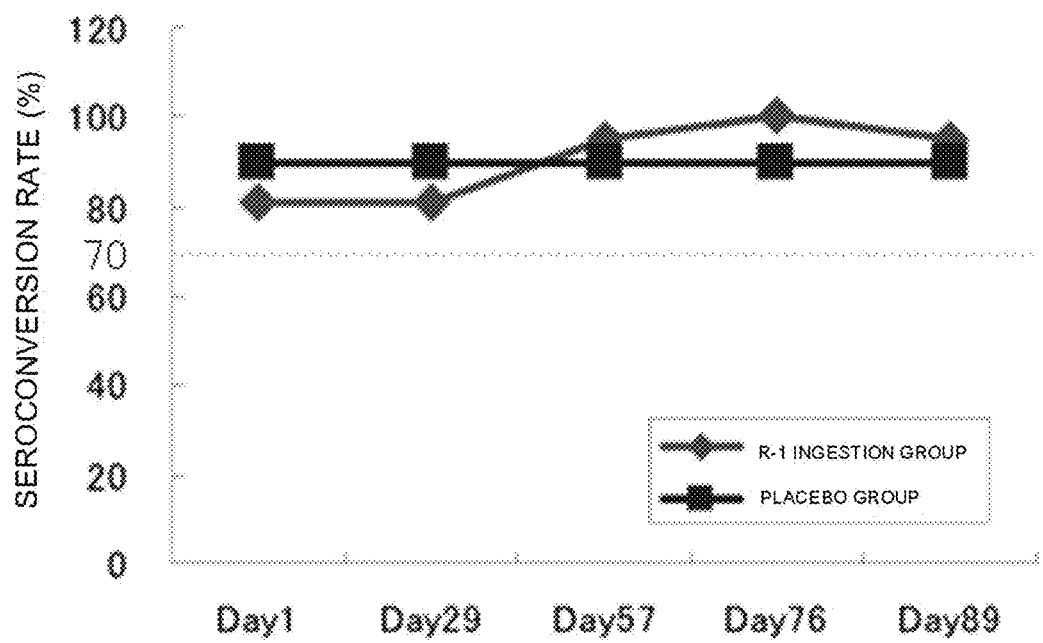
FIG. 3-1 CHANGE IN INFLUENZA A VIRUS H1N1 ANTIBODY PREVALENCE RATE
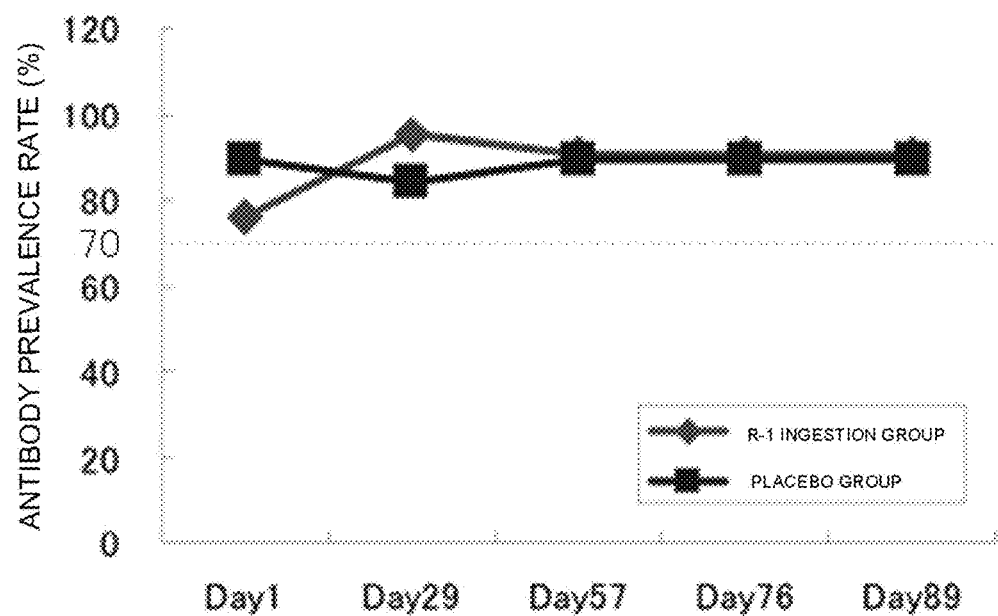
FIG. 3-2 CHANGE IN INFLUENZA A VIRUS H3N2 ANTIBODY PREVALENCE RATE

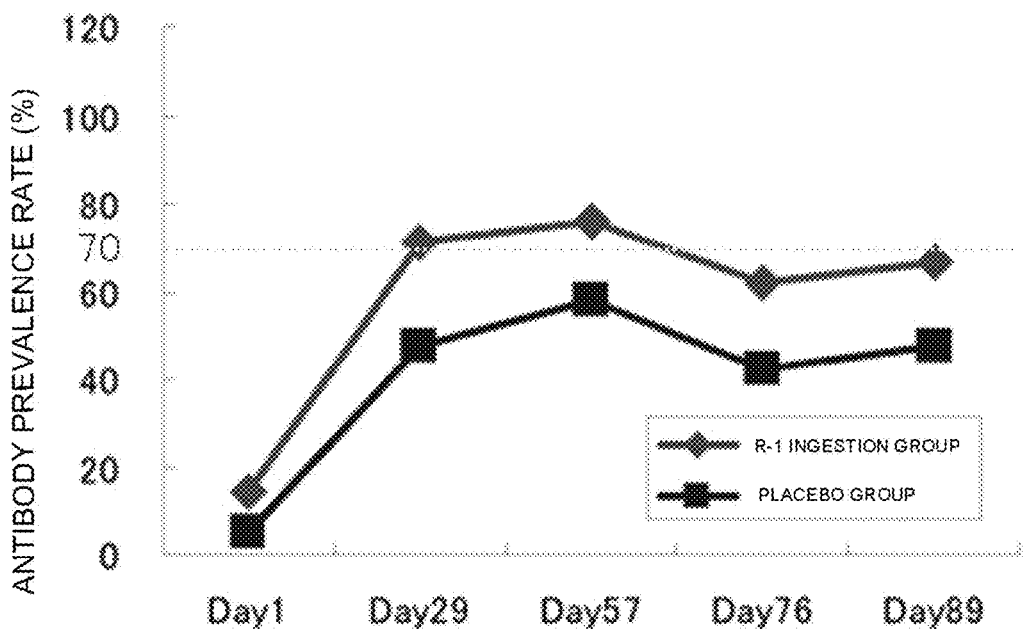
FIG. 3-3 CHANGE IN INFLUENZA B VIRUS ANTIBODY PREVALENCE RATE
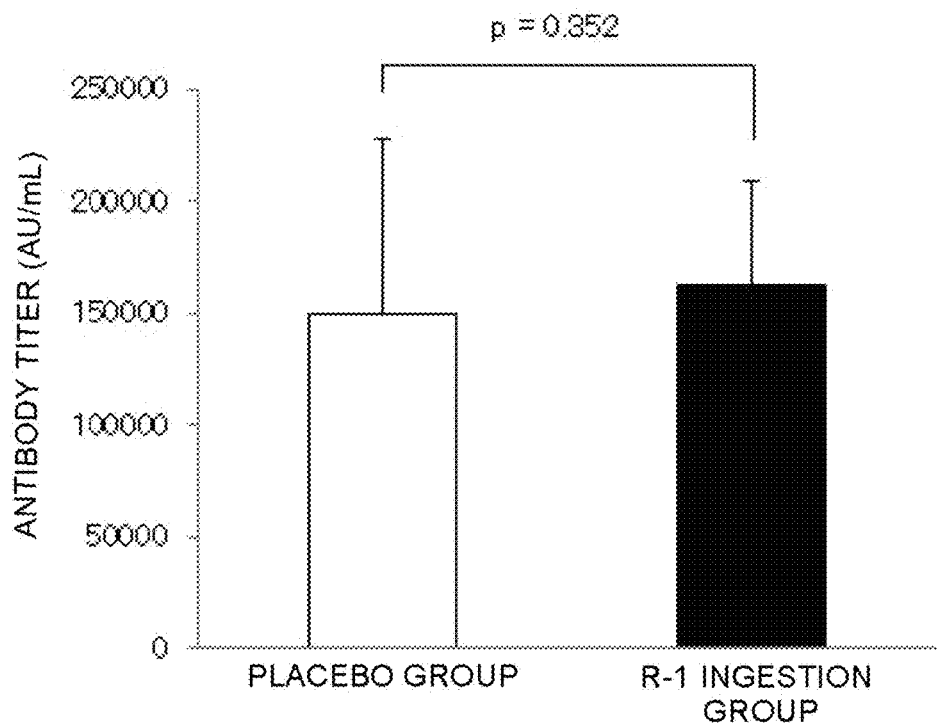
FIG. 4-1 IgG1 ANTIBODY TITER AGAINST OVA ANTIGEN (DAY 14)

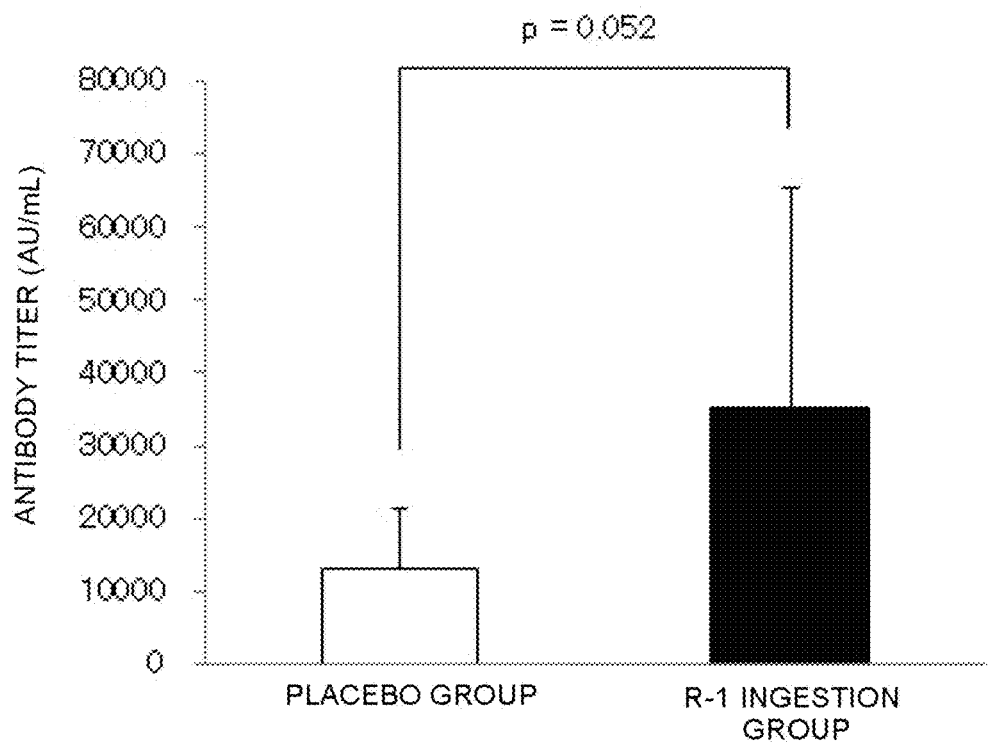
FIG. 4-2 IgG2a ANTIBODY TITER AGAINST OVA ANTIGEN (DAY 14)
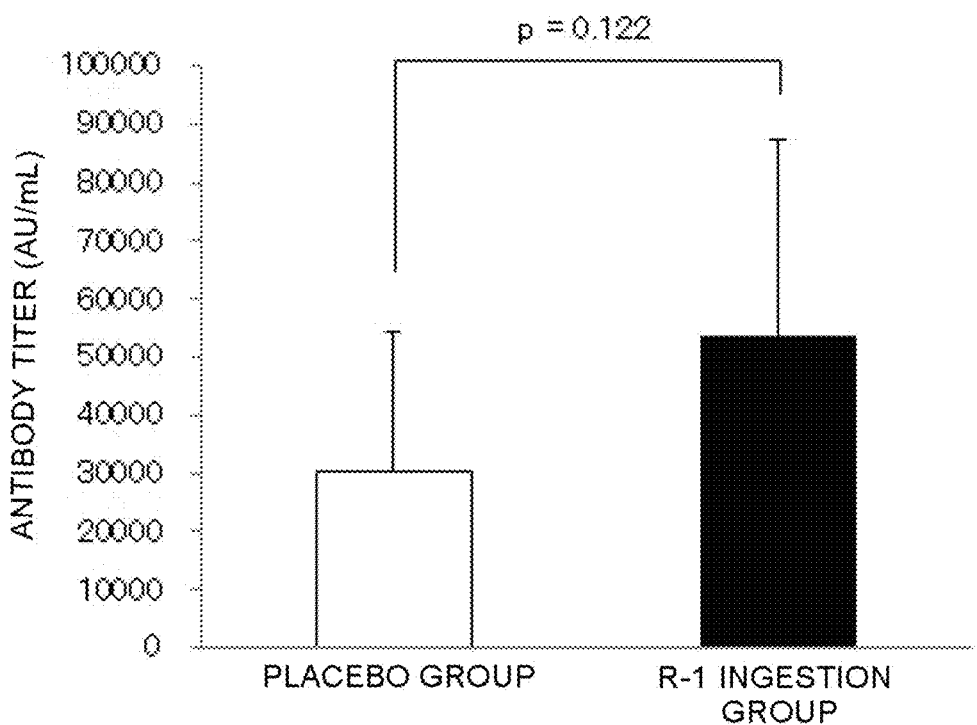
FIG. 4-3 IgG2b ANTIBODY TITER AGAINST OVA ANTIGEN (DAY 14)

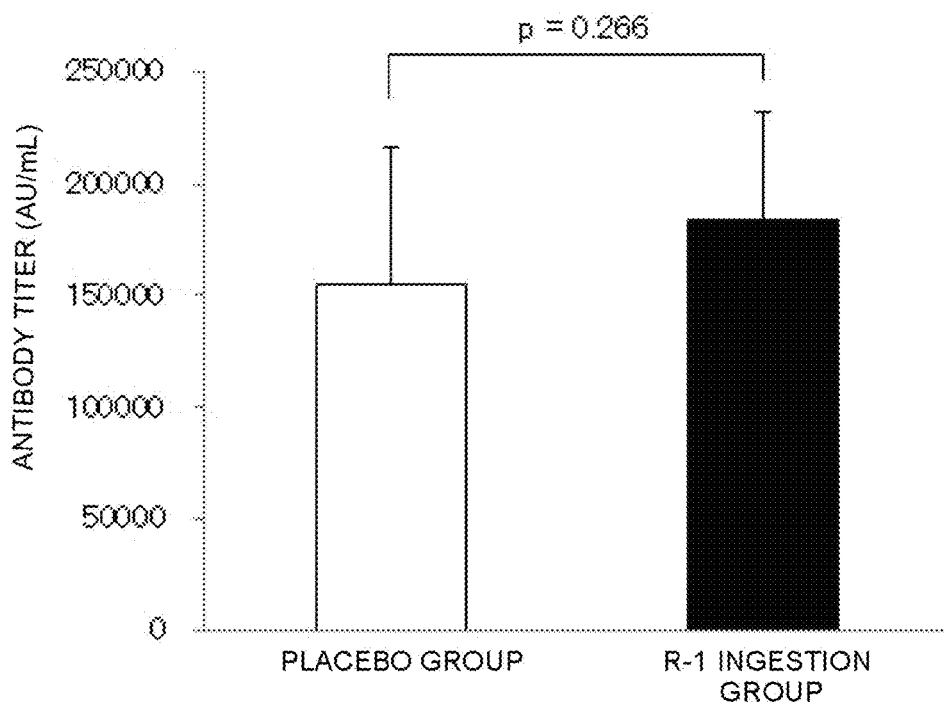
FIG. 5-1 IgG1 ANTIBODY TITER AGAINST OVA ANTIGEN (DAY 21)
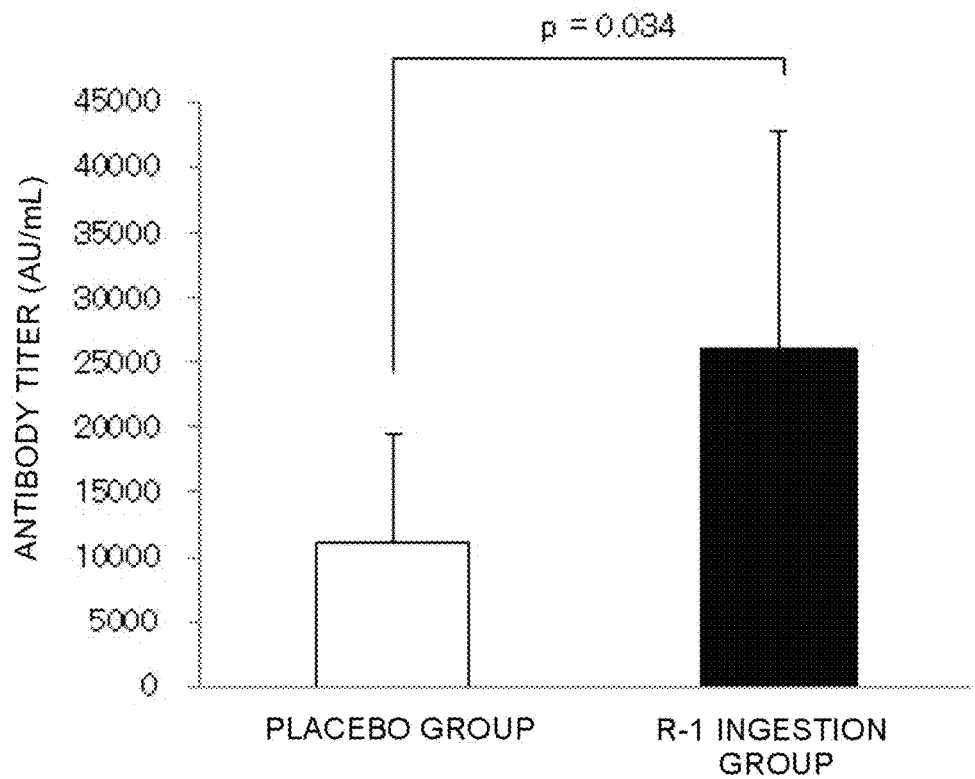
FIG. 5-2 IgG2a ANTIBODY TITER AGAINST OVA ANTIGEN (DAY 21)

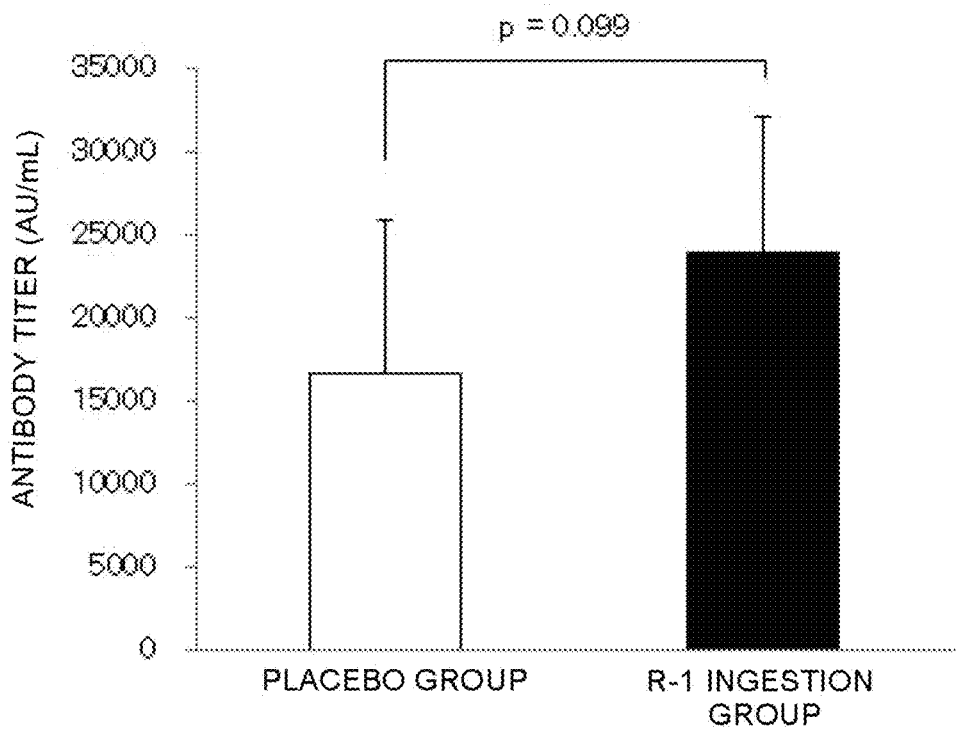
FIG. 5-3 IgG2b ANTIBODY TITER AGAINST OVA ANTIGEN (DAY 21)
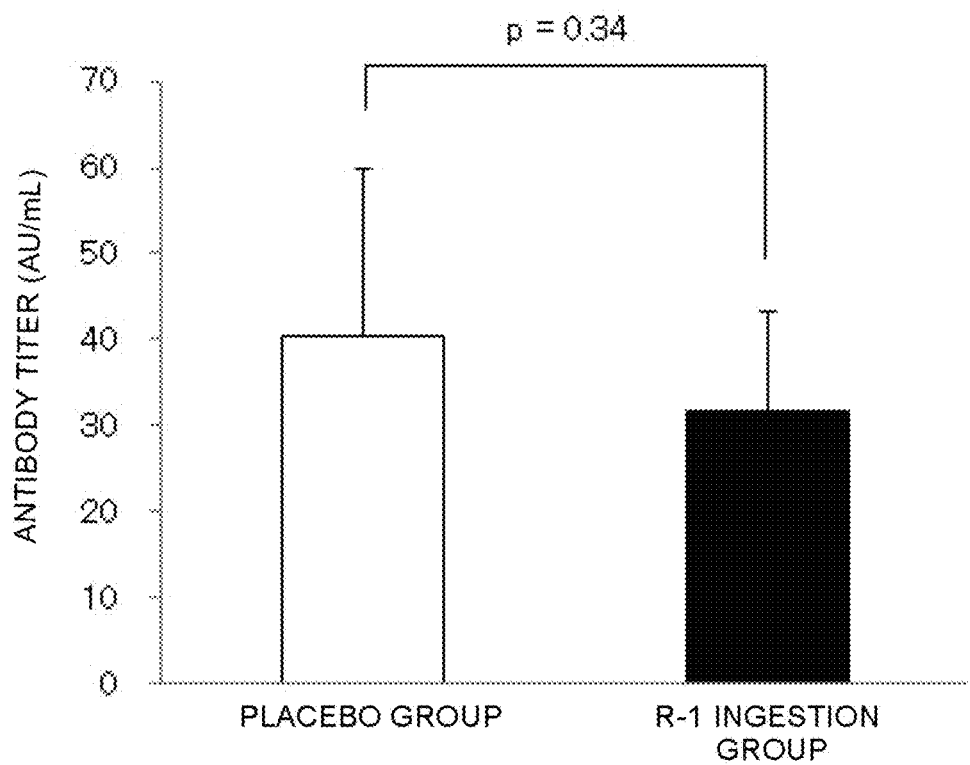
FIG. 5-4 TOTAL IgE ANTIBODY TITER (DAY 21)

ANTIBODY TITER-INCREASING AGENT USING LACTIC ACID BACTERIUM

RELATED APPLICATION

This application is a national stage filing under 35 U.S.C. § 371 of international application PCT/JP2014/072229, filed Aug. 26, 2014, the disclosure of which is incorporated by reference herein in its entirety.

TECHNICAL FIELD

The present invention relates to an antibody titer-increasing agent, for example an adjuvant, using a lactic acid bacterium.

BACKGROUND ART

It is known that for the elderly a respiratory infection such as a cold or influenza, or a gastrointestinal infection such as a norovirus infection can be fatal. Furthermore, in recent years it has been pointed out that for pregnant women there is a risk of her baby developing congenital disease due to rubella infection, and prevention of this infection is needed not only for those who are pregnant but also for people in the community around the pregnant women. Vaccination is useful for the prevention or treatment of various infections in such elderly people, pregnant women, and children and, furthermore, for the prevention or as a counter-measure against serious progression of influenza or bacteria.

Moreover, for a young adult such as a student, the immunological function is usually high, but awareness of protection against infection by means such as vaccination is low; it is known that even for a young adult, immunocompetence is degraded by mental stress, etc. and the person will easily catch an infection, and there is a need to enhance immunocompetence regardless of the age group. However, the antibody titer is not sufficiently increased by vaccination alone, the period during which the effect continues is short, the effect can thus not be fully obtained, and research is being carried out into various vaccine adjuvants.

Vaccine is a general term for antigens that are used to actively immunize humans or animals. There are live vaccines employing an attenuated live pathogen, inactivated or killed vaccines employing a dead virus or pathogenic bacterium, component vaccines employing constituent components thereof, and toxoids, which are inactivated substances of a toxin produced by a bacterium. Furthermore, as vaccines there are cancer vaccines, which are used in the treatment of a cancer, and employ an antigen (cancer antigen) that is not expressed in a normal cell but is specifically expressed only in a cancer cell.

An anti-infection agent containing, as an active ingredient, a fraction that has a molecular weight of at least 1,000 but no greater than 200,000 from water-soluble fractions obtained by fermentation of the rhizome of the Dioscoreaceae Dioscorea plant has been proposed (Patent Document 1).

Furthermore, for the purpose of strengthening immunocompetence, an immunoadjuvant that is nasally administered together with an immunogenic substance and that contains, as an active ingredient, a cultured composition obtained from a culture of a microorganism of the aureobasidium genus (Aureobasidium sp.) has been proposed (Patent Document 2).

Moreover, there have been proposed a food that contains, per 100 g of food, at least $10^6$ counts of Lactobacillus rhamnosus GG and at least 0.5 g of β-glucan isolated from a natural source, and the use thereof as an adjuvant for enhancing the immunoresponse to a vaccine (Patent Document 3).

Furthermore, it has been reported that the antibody titer specific to a vaccine strain increased significantly when a healthy elderly subject of 70 years age or older undertook oral ingestion of a yoghurt drink containing Lactobacillus casei DN-114 001 every day for 4 weeks before being immunized with an influenza vaccine compared with the case of oral ingestion of a placebo non-fermented milk drink (Non-Patent Document 1).

Moreover, it has been reported that influenza-specific IgA was increased by oral ingestion of Lactobacillus fermentum CECT5716 cells (Non-Patent Document 2).

Furthermore, it has been reported that influenza-specific IgG, IgG1, and IgG3 were increased by oral ingestion of a sour milk drink containing Bifidobacterium animalis ssp. lactis (BB-12®) cells and L. paracasei ssp. paracasei (L. casei 431®) (Non-Patent Document 3).

Moreover, it has been reported that acidic polysaccharides produced by Lactobacillus delbrueckii ssp. bulgaricus OLL1073R-1 and fermented milk produced using, as a starter bacterium, Lactobacillus delbrueckii ssp. bulgaricus OLL1073R-1 have an NK cell activation effect (Patent Document 4).

PRIOR ART DOCUMENTS

Patent Documents

[Patent Document 1] JP, A, 04-235921
[Patent Document 2] WO2012/014978
[Patent Document 3] JP, A, 2008-529535
[Patent Document 4] Japanese Patent No. 5177728

Non-Patent Documents

[Non-Patent Document 1] Boge T, Remigy M, Vaudaine S, Tanguy J, Bourdet-Sicard R, Van der Werf S. "A probiotic fermented dairy drink improves antibody response to influenza vaccination in the elderly in two randomized control trials" Vaccine 2009; 27: 5677-5684.

[Non-Patent Document 2] Olivares M, Diaz-Ropero M P, Sierra S, Lara-Villoslada F, Fonolla J, Navas M, Rodriguez J M, Xaus J. "Oral intake of Lactobacillus fermentum CECT5716 enhances the effects of influenza vaccination" Nutrition 2007; 23: 254-260.

[Non-Patent Document 3] Rizzardini et al. "Evaluation of the immune benefits of two probiotic strain Bifidobacterium animalis ssp. lactis, BB-12 and Lactobacillus paracasei ssp. paracasei, L. casei 431 in an influenza vaccination model: a randomized, double-blind, placebo-controlled study" Br. J. Nutr. 107: 876-884. 2012.

[Non-Patent Document 4] Minna K. Salminen, Hilpi Rautelinf, Soile Tynkkynen, Tuiia Poussa, Maiia Saxelinf, Ville Valtonen, and Asko Jarvinen. "Lactobacillus Bacteremia, Clinical Significance, and Patient Outcome, with Special Focus on Probiotic L. Rhamnosus GG" Clinical Infectious Diseases 2004: 38 (1 January): 62-69

[Non-Patent Document 5] Merja Rautio, Hannele Jousimies-Somer, Heikki Kauma, Ilmo Pietarinen, Maija Saxelin, Soile Tynkkynen, and Markku Koskela. "Liver Abscess Due to a Lactobacillus rhamnosus Strain Indistinguishable from L. rhamnosus Strain GG" Clinical Infectious Diseases 1999; 28: 1159-60

SUMMARY OF THE INVENTION

Problems to be Solved by the Invention

As described above, a variety of research and investigative work has been carried out, but none thereof can be said to be a safe and simple adjuvant, and the practicality is not necessarily sufficient.

The invention described in Patent Document 1 requires steps of long-term culturing, filtration, etc., the production method is complicated, and the effect on antibody titer is unknown. Furthermore, the invention described in Patent Document 2 carries out vaccination at the same time as nasal or oral administration of a culture of a microorganism of the *aureobasidium* genus itself, and it does not enable easy ingestion of an adjuvant. Moreover, in the invention described in Patent Document 3, *Lactobacillus rhamnosus* GG is used, and the growth rate of *Lactobacillus rhamnosus* GG is increased using β-glucan; it is stated that *Lactobacillus rhamnosus* GG is useful as a vaccine adjuvant, but the adjuvant effect is not studied, and a probiotic that can be used as a starter bacterium for fermented milk is not provided. Furthermore, cases of sepsis and liver abscess have been reported with *Lactobacillus rhamnosus* GG (Non-Patent Document 4 and Non-Patent Document 5).

Moreover, Non-Patent Document 1 relates to a yoghurt drink containing *Lactobacillus casei* DN-114 001, for which an adjuvant effect for an influenza vaccine has been shown, but the fermentation thereof requires separate *Lactobacillus delbrueckii* ssp. *bulgaricus* and *Streptococcus thermophilus*. Furthermore, in Non-Patent Documents 2 and 3, it is unclear whether or not *Lactobacillus fermentum* CECT5716, *B. animalis* ssp. *lactis* (BB-12®), and *L. paracasei* ssp. *paracasei* (*L. casei* 431®, for each of which an adjuvant effect for an influenza vaccine has been shown, can be used as a starter for fermented milk.

Moreover, the invention described in Patent Document 4 relates to an acidic polysaccharide produced by *Lactobacillus delbrueckii* ssp. *bulgaricus* OLL1073R-1 and fermented milk produced using as a starter bacterium *Lactobacillus delbrueckii* ssp. *bulgaricus* OLL1073R-1; the effect studied here is the activation of NK cells, and the effect on antibody titer is unknown.

As described above, various adjuvants have been proposed, but there is still no adjuvant that has a continuing effect in enhancing the antibody titer increase due to vaccination, and that is safe, can be easily produced, and can be ingested freely regardless of the age group.

Therefore, it is an object of the present invention to provide an antibody titer-increasing agent, for example an adjuvant, that can continue the effect due to vaccination, and that is safe and economical and can be ingested freely regardless of the age group, and a method for producing same.

Means for Solving the Problems

While carrying out an intensive investigation in order to solve the above problems, the present inventors have found that *Lactobacillus delbrueckii* ssp. *bulgaricus* OLL1073R-1, which can be used as a starter for fermented milk, has an effect in increasing antibody titer, for example an adjuvant effect, and as a result of further research the present invention has been accomplished.

That is, the present invention relates to the following.

[1]
An antibody titer-increasing agent comprising *Lactobacillus delbrueckii* ssp. *bulgaricus* OLL1073R-1 and/or a culture thereof.

[2]
The antibody titer-increasing agent according to [1], wherein it is an adjuvant.

[3]
The antibody titer-increasing agent according to [2], wherein it is an adjuvant for a vaccine.

[4]
The antibody titer-increasing agent according to [3], wherein it is an adjuvant for a vaccine for an infectious disease.

[5]
The antibody titer-increasing agent according to [4], wherein the infectious disease is influenza.

[6]
The antibody titer-increasing agent according to any one of [1] to [5], wherein the culture is a composition obtained by culturing *Lactobacillus delbrueckii* ssp. *bulgaricus* OLL1073R-1 and *Streptococcus thermophilus*.

[7]
The antibody titer-increasing agent according to any one of [1] to [6], wherein it comprises $9 \times 10^7$ to $10^{12}$ cfu lactic acid bacteria, including *Lactobacillus delbrueckii* ssp. *bulgaricus* OLL1073R-1, per package.

[8]
The antibody titer-increasing agent according to any one of [1] to [7], wherein it comprises 10 to 1000 g or 10 to 1000 mL per package.

[9]
A product formed by packaging the antibody titer-increasing agent according to any one of [1] to [8].

[10]
A method (excluding a medical intervention) for increasing an antibody titer, the method comprising a subject ingesting or being made to ingest the antibody titer-increasing agent according to any one of [1] to [8].

[11]
The method according to [10], wherein ingestion of 10 to 1000 g or 10 to 1000 mL of the antibody titer-increasing agent per day is continued for at least three weeks.

[12]
The method according to [11], wherein ingestion of the antibody titer-increasing agent is continued from at least one week before the date of vaccination.

The present invention also relates to the following.

[I]
An adjuvant comprising *Lactobacillus delbrueckii* ssp. *bulgaricus* OLL1073R-1 and/or a culture thereof.

[II]
The adjuvant according to [I], wherein it is for use in an influenza vaccine.

[III]
The adjuvant according to [I] or [II], wherein the culture is a culture obtained using *Lactobacillus delbrueckii* ssp. *bulgaricus* OLL1073R-1 and *Streptococcus thermophilus*.

[IV]
The adjuvant according to any one of [I] to [III], wherein it comprises $9 \times 10^7$ cfu of lactic acid bacteria, including *Lactobacillus delbrueckii* ssp. *bulgaricus* OLL1073R-1, per package.

[V]
The adjuvant according to any one of [I] to [VI], wherein it comprises 10 to 1000 g or 10 to 1000 mL per package.

[VI]
A method (excluding medical intervention) for enhancing a vaccine effect, the method comprising a subject ingesting or being made to ingest the adjuvant according to any one of [I] to [V].

[VII]
The method according to [VI], wherein ingestion of 10 to 1000 g or 10 to 1000 mL of the culture per day is continued for at least 3 weeks.

[VIII]
A method (excluding medical intervention) for increasing antibody titer, the method comprising a subject ingesting or being made to ingest *Lactobacillus delbrueckii* ssp. *bulgaricus* OLL1073R-1 and/or a culture thereof.

[IX]
The method according to [VIII], wherein the culture is a culture obtained using *Lactobacillus delbrueckii* ssp. *bulgaricus* OLL1073R-1 and *Streptococcus thermophilus*.

[X]
The method according to [VIII] or [IX], wherein the antibody titer is an influenza antibody titer.

[XI]
The method according to any one of [VIII] to [X], wherein ingestion of 10 to 1000 g or 10 to 1000 mL of the culture per day is continued for at least 3 weeks.

Effects of the Invention

The present invention enables *Lactobacillus delbrueckii* ssp. *bulgaricus* OLL1073R-1 and/or a culture thereof to be used in the medical prevention or treatment of a disease and to be also used in the maintenance and promotion of health as a food for specified health use or as a general food. In particular, it can increase antibody titer and maintain it at a high level and can enhance a vaccine effect. Furthermore, since *Lactobacillus delbrueckii* ssp. *bulgaricus* OLL1073R-1 is a strain that can be used as a starter bacterium for fermented milk, it is possible to provide by use thereof an antibody titer-increasing agent, for example an adjuvant, that is safe, can be produced simply, and can be ingested freely regardless of the age group.

BRIEF DESCRIPTION OF DRAWINGS

FIG. 1-1 A diagram showing change in influenza A virus H1N1 antibody titer.

FIG. 1-2 A diagram showing change in influenza A virus H3N2 antibody titer.

FIG. 1-3 A diagram showing change in influenza B virus antibody titer.

FIG. 2-1 A diagram showing change in influenza A virus H1N1 seroconversion rate.

FIG. 2-2 A diagram showing change in influenza A virus H3N2 seroconversion rate.

FIG. 2-3 A diagram showing change in influenza B virus seroconversion rate.

FIG. 3-1 A diagram showing change in influenza A virus H1N1 antibody prevalence rate.

FIG. 3-2 A diagram showing change in influenza A virus H3N2 antibody prevalence rate.

FIG. 3-3 A diagram showing change in influenza B virus antibody prevalence rate.

FIG. 4-1 A diagram showing IgG1 antibody titer against OVA antigen 1 week after second ovalbumin (OVA) immunization of mouse (Day 14).

FIG. 4-2 A diagram showing IgG2a antibody titer against OVA antigen 1 week after second OVA immunization of mouse (Day 14).

FIG. 4-3 A diagram showing IgG2b antibody titer against OVA antigen 1 week after second OVA immunization of mouse (Day 14).

FIG. 5-1 A diagram showing IgG1 antibody titer against OVA antigen 2 weeks after second OVA immunization of mouse (Day 21).

FIG. 5-2 A diagram showing IgG2a antibody titer against OVA antigen 2 weeks after second OVA immunization of mouse (Day 21).

FIG. 5-3 A diagram showing IgG2b antibody titer against OVA antigen 2 weeks after second OVA immunization of mouse (Day 21).

FIG. 5-4 A diagram showing total IgE antibody titer 2 weeks after second OVA immunization of mouse (Day 21).

MODES FOR CARRYING OUT THE INVENTION

Figure 6:
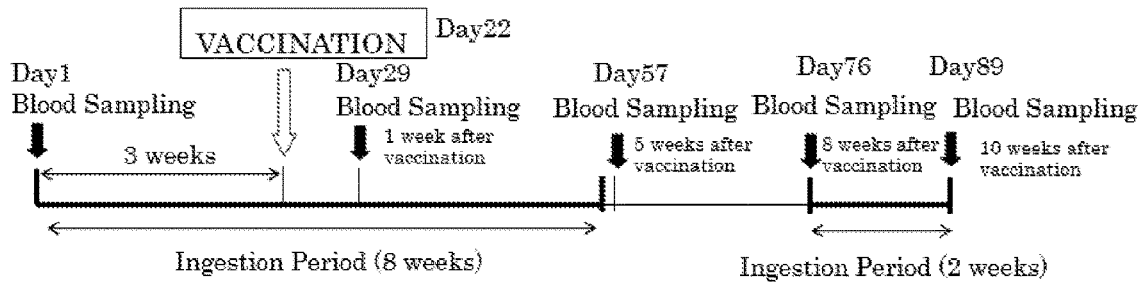
FIG. 6 A diagram showing schedules for ingestion, vaccination, and blood sampling.

'*Lactobacillus delbrueckii* ssp. *bulgaricus* OLL1073R-1' in the present specification was deposited in Japan on 22 Feb. 1999 with the International Patent Organism Depositary, National Institute of Advanced Industrial Science and Technology (IPOD, AIST) (6 Chuo, 1-1-1 Higashi, Tsukuba, Ibaraki, Japan Post code 305-8566) with accession number: FERM P-17227 (identification reference: *Lactobacillus delbrueckii* ssp. *bulgaricus* OLL1073R-1, deposition date (accession date): 19 Feb. 1999), transferred to international deposition based on the Budapest Treaty on 29 Nov. 2006, and designated with accession number FERM BP-10741.

In addition, as described in Budapest Notification No. 282 (http://www.wipo.int/treaties/en/notifications/budapest/treaty_budapest_282.html), since the National Institute of Technology and Evaluation (IPOD, NITE) acquired the patent organism depository business from the International Patent Organism Depository, National Institute of Advanced Industrial Science and Technology (IPOD, AIST), it is now deposited with the National Institute of Technology and Evaluation (IPOD, NITE) (room 120, 2-5-8 Kazusakamatari, Kisarazu, Chiba) (accession number FERM BP-10741).

*Lactobacillus delbrueckii* ssp. *bulgaricus* OLL1073R-1 and/or a culture thereof can increase an antibody titer and maintain it at a high level.

The 'culture' referred to in the present specification means a composition obtained by culturing *Lactobacillus delbrueckii* ssp. *bulgaricus* OLL1073R-1, and includes materials in any state obtained by treating a culture, such as a culture itself obtained by culturing bacterial cells, a culture from which bacterial cells are separated and removed by centrifuging, etc., a culture concentrate, a culture dilution, and a solid obtained by removing water content from a culture. In addition, in the present specification 'culturing' includes fermentation by means of *Lactobacillus delbrueckii* ssp. *bulgaricus* OLL1073R-1, and a 'culture' includes a product fermented by means of *Lactobacillus delbrueckii* ssp. *bulgaricus* OLL1073R-1, that is, *Lactobacillus delbrueckii* ssp.

Culturing of *Lactobacillus delbrueckii* ssp. *bulgaricus* OLL1073R-1 may be carried out in accordance with a standard method. For example, bacterial cells may be inoculated in a medium containing raw milk (unpasteurized milk), pasteurized milk, full fat condensed milk, whole milk powder, skimmed milk, skimmed condensed milk, skimmed milk powder, milk protein concentrate (MPC), whey, whey powder, desalted whey, desalted whey powder, whey protein concentrate (WPC), whey protein isolate (WPI), α-lactoalbumin (α-La), β-lactoglobulin (β-Lg), casein, sodium caseinate, calcium caseinate, cream, butter, saccharides (including lactose), a mineral, a vitamin, and/or a yeast extract, and anaerobically cultured at a temperature of 35° C. to 45° C. for 2 to 24 hours. As a typical medium, whey is processed with a protease, a yeast extract is added thereto and, furthermore, the pH is adjusted to on the order of 7.

In one embodiment of the present invention, the culturing temperature for *Lactobacillus delbrueckii* ssp. *bulgaricus* OLL1073R-1 is preferably in the range of 30° C. to 45° C. It is particularly preferably in the range of 32° C. to 44° C., and yet more preferably in the range of 34° C. to 43° C.

In one embodiment of the present invention, the culturing time for *Lactobacillus delbrueckii* ssp. *bulgaricus* OLL1073R-1 is preferably in the range of 1 to 24 hours. It is particularly preferably in the range of 2 to 12 hours, and yet more preferably in the range of 3 to 8 hours.

In addition, in one embodiment of the present invention, the culturing temperature and the culturing time may be in any combination, but from the viewpoint of production efficiency, the number of cells of *Lactobacillus delbrueckii* ssp. *bulgaricus* OLL1073R-1, the acidity and flavor of the culture (fermented product), etc., culturing (fermentation) is carried out preferably at 30° C. to 45° C. for 1 to 24 hours, more preferably at 32° C. to 44° C. for 2 to 12 hours, and yet more preferably at 34° C. to 43° C. for 3 to 8 hours.

In one embodiment of the present invention, from the viewpoint of production efficiency, the culture is preferably a culture obtained using *Lactobacillus delbrueckii* ssp. *bulgaricus* OLL1073R-1 and *Streptococcus thermophilus*, for example a composition obtained by culturing *Lactobacillus delbrueckii* ssp. *bulgaricus* OLL1073R-1 and *Streptococcus thermophilus*. In the present invention, any strain of *Streptococcus thermophilus* may be used, and *Streptococcus thermophilus* OLS3059 may preferably be used.

The '*Streptococcus thermophilus* OLS3059' in the present specification was deposited in Japan on 29 Feb. 1996 with the International Patent Organism Depository, National Institute of Advanced Industrial Science and Technology (IPOD, AIST) (6 Chuo, 1-1-1 Higashi, Tsukuba, Ibaraki, Japan Post code 305-8566) with the accession number: FERM P-17227 (identification reference: *Streptococcus thermophilus* OLS3059, deposition date (accession date): 29 Feb. 1996), transferred to international deposition based on the Budapest Treaty on 29 Nov. 2006, and designated with the accession number FERM BP-10740.

In addition, as described in Budapest Notification No. 282 (http://www.wipo.int/treaties/en/notifications/budapest/treaty_budapest_282.html), since the National Institute of Technology and Evaluation (IPOD, NITE) acquired the patent organism depository business from the International Patent Organism Depository, National Institute of Advanced Industrial Science and Technology (IPOD, AIST), it is now deposited with the National Institute of Technology and Evaluation (IPOD, NITE) (room 120, 2-5-8 Kazusakamatari, Kisarazu, Chiba)(accession number FERM BP-10740).

The 'antibody titer' referred to in the present specification means an indicator showing the amount of antibodies produced against an antigen, and it may typically be measured by a method such as a hemagglutination inhibition test (HI method), an enzyme-linked immunosorbent assay (ELISA), an enzyme immunoassay (EIA), or a latex turbidimetric immunoassay (LTI).

Examples of the antibody titer include, but are not limited to, an antibody titer against a viral or bacterial infection pathogen such as influenza, measles, epidemic mumps, rubella, varicella, diphtheria, tetanus, or pertussis, and an antibody titer against a cancer antigen such as prostate cancer. Preferred examples include an antibody titer against a disease pathogen that can be prevented or treated by a vaccine and an antibody titer for a virus pathogen of a viral disease, and particularly preferred examples include an antibody titer against an infection pathogen, for which vaccination is recommended, such as influenza, measles, or rubella.

The 'antibody' referred to in the present specification means a molecule that is a glycoprotein molecule produced, among lymphocytes, by B cells and that has the function of recognizing and binding to an antigen. Furthermore, antibodies are divided into several classes (isotypes) according to the structure of a constant region. In mammals, immunoglobulins are classified into the five classes of IgG, IgA, IgM, IgD, and IgE according to differences in the structure of the constant region, and each class is further classified into subclasses. The 'antibody' referred to in the present specification means a general term for the classes and subclasses.

The effector function of an antibody is the function possessed by the Fc region of the antibody and depends greatly on the antibody class. Complement-activating potency is limited to antibodies of the IgM and IgG classes, and the function of lysing a cell to which the variable region of an antibody binds is particularly called CDC (complement-dependent cytotoxicity). Furthermore, the Fc regions of the antibodies of the IgG, IgE, and IgA classes each bind to specific Fc receptors and function to activate cells having an Fc receptor or transport the antibodies between cells. In particular, the action of the IgG class antibody of activating effector cells of T cells, NK cells, neutrophils, or macrophages via an Fc receptor thereof and killing target cells to which the variable region of the antibody binds is called ADCC (antibody-dependent cell-mediated cytotoxicity).

In one embodiment of the present invention, the 'antibody titer' is an IgG antibody titer.

The present invention provides a method for increasing an antibody titer, the method comprising ingesting or making be ingested *Lactobacillus delbrueckii* ssp. *bulgaricus* OLL1073R-1 and/or a culture thereof. Here, the method for increasing an antibody titer includes a medical intervention by a physician and a non-medical intervention.

The 'ingestion' referred to in the present specification means taking into the body, and examples including drinking/eating, inhaling, and tube feeding. Typical examples include, but are not limited to, oral ingestion and enteral ingestion.

In one embodiment of the present invention, oral ingestion, and in particular ingestion by drinking/eating, is preferable.

The 'subject' referred to in the present specification means a subject to which the antibody titer-increasing agent, for example an adjuvant, of the present invention is applied; examples include a mammal such as a human, and a human is preferable.

The 'making be ingested' referred to in the present specification means making a subject ingest directly or indirectly by visibly and/or audibly advocating it for a specific purpose or effect, and examples include an act of proposing, suggesting, or directing a subject to ingest by advocating it for a specific purpose or effect, the act being carried out by a manufacturer toward a seller or a consumer or by a seller toward a consumer.

Furthermore, the present invention provides an antibody titer-increasing agent containing *Lactobacillus delbrueckii* ssp. *bulgaricus* OLL1073R-1 and/or a culture thereof.

The 'antibody titer-increasing agent' referred to in the present specification means a substance that induces the production of an antibody, increases the antibody titer, and maintains it at a high level, and a composition containing same.

In the present invention, the antibody titer-increasing agent includes *Lactobacillus delbrueckii* ssp. *bulgaricus* OLL1073R-1 itself, a *Lactobacillus delbrueckii* ssp. *bulgaricus* OLL1073R-1 culture itself, and a composition containing same.

In the present invention, the antibody titer-increasing agent may be in any form as long as it is suitable for ingestion. Examples include, but are not limited to, pharmaceuticals, quasi-drugs, food with health claims, food for specified health use, food with nutrient function claims, general food, health supplement food, health food, supplements, enteral nutrients, oral cosmetics, and feedstuffs.

In one embodiment of the present invention, the antibody titer-increasing agent may be in the form of a fermented milk itself from the viewpoint of palatability.

In a preferred embodiment of the present invention, the antibody titer-increasing agent is a yoghurt such as plain yoghurt, hard yoghurt, soft yoghurt, or drinking yoghurt from the viewpoint of production efficiency.

In one embodiment of the present invention, from the viewpoint of ease of storage, it may be in the form of granules, a lozenge, a tablet, a capsule, etc.

In one embodiment of the present invention, when *Lactobacillus delbrueckii* ssp. *bulgaricus* OLL1073R-1 and/or a culture thereof is in the form of a liquid, from the viewpoint of ease of ingestion and effect in increasing the antibody titer, it is desirable to ingest 5 to 1000 mL, preferably 50 to 500 mL, and more preferably 100 to 200 mL per day.

In one embodiment of the present invention, when *Lactobacillus delbrueckii* ssp. *bulgaricus* OLL1073R-1 and/or a culture thereof is in the form of a solid or a semi-solid, from the viewpoint of ease of ingestion and effect in increasing the antibody titer it is desirable to ingest 5 to 1000 g, preferably 50 to 500 g, and more preferably 100 to 200 g per day.

In one embodiment of the present invention, when *Lactobacillus delbrueckii* ssp. *bulgaricus* OLL1073R-1 and/or a culture thereof is in the form of a dried product, it is desirable from the viewpoint of ease of ingestion and effect in increasing the antibody titer to ingest 0.1 to 50 g, preferably 0.5 to 10 g, and more preferably 1 to 5 g per day.

In one embodiment of the present invention, an antibody titer-increasing agent that can exhibit a stable antibody titer-increasing effect can be provided by putting an appropriate amount for one ingestion into a configuration of one package.

In one embodiment of the present invention, the antibody titer-increasing agent can be made into one package with the aforementioned appropriate amount for one day of ingestion.

Therefore, in one embodiment of the present invention, the antibody titer-increasing agent can be an antibody titer-increasing agent containing the aforementioned amount of *Lactobacillus delbrueckii* ssp. *bulgaricus* OLL1073R-1 and/or a culture thereof.

The present invention also provides a product formed by packaging the antibody titer-increasing agent. Such a packaged product can be a product formed by individually packaging a quantity appropriate for one ingestion, a product formed by packaging together a quantity appropriate for ingestions over a plurality of days, for example, one week, or a product containing a plurality of individual packages, etc.

In one embodiment of the present invention, the antibody titer-increasing agent contains, per individual package, lactic acid bacteria containing at least $9\times10^7$ cfu, preferably at least $9\times10^8$ cfu, and more preferably at least $9\times10^9$ cfu of *Lactobacillus delbrueckii* ssp. *bulgaricus* OLL1073R-1.

Alternatively, in one embodiment of the present invention, the antibody titer-increasing agent contains, per individual package, lactic acid bacteria containing $9\times10^7$ to $10^{12}$ cfu, preferably $9\times10^8$ to $10^{12}$ cfu, and more preferably $9\times10^9$ to $10^{11}$ cfu of *Lactobacillus delbrueckii* ssp. *bulgaricus* OLL1073R-1.

In the present specification, the 'individual package' includes all configurations, and examples include general package configurations such as a lidded container, a capped bottle, an individual bag, a pouch, a tube, a blister pack, and an ampoule. Furthermore, it includes a package configuration that can be ingested in its entirety such as a capsule or an edible film such as a wafer.

In the present specification, the 'packaging' includes packaging in any package configuration as described above.

In one embodiment of the present invention, each individual package or a package containing a plurality of individual packages can have written thereon an explanation of the application, efficacy, and function of the product, the type of active ingredient, the type of functional component, the ingestion method, etc., and/or can be packaged with a written material such as for example a written explanation or a written attachment, and/or can be presented separately with a written material such as a pamphlet, thus enabling its application to be clarified.

In one embodiment of the present invention, the antibody titer-increasing agent of the present invention preferably has displayed thereon an explanation of the application, efficacy, and function of the agent, the type of active ingredient, the type of functional component, the ingestion method, etc. The 'display' can be a display suitable for each of a pharmaceutical, quasi drug, food with health claims, food for specified health use, food with nutrient function claims, general food, health aid food, health food, supplement, enteral nutrient, oral cosmetic, and feedstuff.

In the present specification, 'display' includes all types of display for advising a consumer of the above explanation and includes any display regardless of the purpose of the display, the contents of the display, the subject or medium via which the display is carried out, etc. as long as the contents of display described above can be recalled or inferred. Examples include display of the above explanation on a package or container of a product, exhibition or distribution of a display of the explanation on an advertisement, price list, or transaction document related to a product, and providing information with the above as contents by an electromagnetic (internet, etc.) method.

In one embodiment of the present invention, when the antibody titer-increasing agent is for example a food or a drink, the product formed by packaging the antibody titer-increasing agent is preferably a food or drink on which the application purpose is displayed as being for increasing the antibody titer, a food or drink having an antibody titer-increasing effect and displayed with for example 'for increasing antibody titer', a food or drink containing *Lactobacillus delbrueckii* ssp. *bulgaricus* OLL1073R-1 and displayed with 'for increasing antibody titer', or a food or drink containing *Lactobacillus delbrueckii* ssp. *bulgaricus* OLL1073R-1 and displayed with 'for improving immunocompetence', etc.

The words used in order to carry out the display as described above are not limited only to words such as for example 'for increasing antibody titer' or 'for improving immunocompetence', and needless to say words other than the above are also within the scope of the present invention as long as those words are expressing an antibody titer-increasing effect. As such words, for example, there can be a display based on various application purposes that enable a consumer to recognize an antibody titer-increasing effect.

On the other hand, the displayed contents are preferably a display that is permitted by an administrative body, etc. (for example, a display that has received permission based on various types of institution registered by an administrative body and is carried out in a mode based on such a permission), and such displayed contents are preferably attached to a package, a container, a catalog, a pamphlet, advertising material in a sales place such as a POP, another document, etc.

Furthermore, examples include displays as a pharmaceutical, a quasi drug, food with health claims, food for specified health use, food with nutrient function claims, general food, health aid food, health food, supplement, enteral nutrient, oral cosmetic, feedstuffs, etc. In particular, examples include a display related to functionality, etc. permitted by the institution of each country, such as for example a display permitted by the Consumer Affairs Agency in Japan or a display permitted by an institution relating to food for specified health use or an institution similar thereto. Examples include a display as food for specified health use, a display as food for conditional specified health use, a display stating that an effect is given to the structure or function of the body, and a display relating to a reduction in the risk of a disease; in further detail, typical examples can include a display as food for specified health use specified by the Health Promotion Act (in particular, a display relating to the health application) and a display analogous thereto.

In one embodiment of the present invention, it is desirable that in order to enhance the antibody titer-increasing effect ingestion of *Lactobacillus delbrueckii* ssp. *bulgaricus* OLL1073R-1 and/or a culture thereof, or an antibody titer-increasing agent containing same is continued for at least 3 weeks, preferably at least 5 weeks, and more preferably at least 8 weeks.

Since *Lactobacillus delbrueckii* ssp. *bulgaricus* OLL1073R-1 and/or a culture thereof can be ingested safely, the upper limit for the ingestion period is not particularly limited, and it can be continued permanently. From the viewpoint of obtaining a sufficiently effective antibody titer-increasing effect, up to about 12 weeks may be used as a guideline.

In one embodiment of the present invention, the antibody titer-increasing agent is an adjuvant.

In the present specification, the 'adjuvant' is typically an immunological adjuvant and is a component that enhances the antibody-producing ability due to administration of an antigen when inducing immunity, or a composition containing same.

In the present invention, the 'adjuvant' includes *Lactobacillus delbrueckii* ssp. *bulgaricus* OLL1073R-1 itself, a *Lactobacillus delbrueckii* ssp. *bulgaricus* OLL1073R-1 culture itself, and a composition containing same.

In the present invention, the adjuvant can take any configuration, and examples thereof include, but are not limited to, a pharmaceutical, a quasi drug, a food with health claims, a food for specified health use, a food with nutrient function claims, a general food, a health aid food, a health food, a supplement, an enteral nutrient, an oral cosmetic, and a feedstuff.

In one embodiment of the present invention, the adjuvant can take the configuration of a fermented milk itself from the viewpoint of palatability.

In a preferred embodiment of the present invention, from the viewpoint of production efficiency, the adjuvant is a yoghurt such as plain yoghurt, hard yoghurt, soft yoghurt, or drinking yoghurt.

In one embodiment of the present invention, from the viewpoint of storage stability, etc. it may take a configuration such as a lozenge, a tablet, or a capsule.

The effect of a vaccine may be enhanced by ingesting the antibody titer-increasing agent, for example an adjuvant, of the present invention or by making it be ingested.

In the present specification, the 'vaccine' means a pharmaceutical composition used for the prevention and treatment of an infection. Furthermore, the vaccine includes a cancer antigen, and also includes a vaccine that is used as a cancer vaccine in the treatment of a cancer. The vaccine may contain one or more pathogenically dead or weakened pathogens, cancer antigens, and optionally one or more additives such as a general adjuvant or carrier.

Specific examples of the vaccine include, but are not limited to, an influenza vaccine, a measles vaccine, an epidemic parotitis vaccine, a rubella vaccine, an MR vaccine, an MMR vaccine, a varicella vaccine, an MMRV vaccine, a diphtheria vaccine, a tetanus vaccine, a pertussis vaccine, a DTP vaccine, an inactivated polio virus vaccine, a hepatitis B virus vaccine, a meningococcal conjugate vaccine, an RS virus vaccine, a human papilloma virus vaccine, and a cancer vaccine.

In the present specification, the 'vaccine effect being enhanced' means that an antibody titer specific to a vaccine strain increases.

In the present specification, a 'method for enhancing a vaccine effect' includes both a medical intervention by a physician and a non-medical intervention.

The antibody titer-increasing agent, for example an adjuvant, of the present invention may take a configuration of a mixture with a vaccine or an individual configuration in which it is separate from a vaccine. In one embodiment of the present invention, it is preferable to take an individual configuration separate from a vaccine since there are the advantages that long term ingestion becomes possible, combination with various types and configurations of vaccine becomes possible, etc.

The antibody titer-increasing agent, for example an adjuvant, of the present invention may be ingested at the same time as immunization with a vaccine or may be ingested before or after vaccination.

In one embodiment of the present invention, in order to enhance the antibody titer-increasing effect, for example an adjuvant effect, it is preferable to ingest the antibody titer-increasing agent, for example an adjuvant, for at least 4 weeks, preferably at least 6 weeks, and more preferably at least 8 weeks before and/or after vaccination.

In one embodiment of the present invention, in order to enhance the antibody titer-increasing effect, for example an adjuvant effect, the antibody titer-increasing agent, for example an adjuvant, is ingested at least 1 week, preferably at least 2 weeks, and more preferably at least 3 weeks prior to the date of vaccination.

In one embodiment of the present invention, in order to enhance the antibody titer-increasing effect, for example an adjuvant effect, the antibody titer-increasing agent, for example an adjuvant, is continuously ingested for at least 1 week, preferably at least 3 weeks, and more preferably at least 5 weeks from the date of vaccination.

In one embodiment of the present invention, when the antibody titer-increasing agent, for example an adjuvant, is a liquid, it is preferable to ingest 10 to 1000 mL, more preferably 50 to 500 mL, and yet more preferably 100 to 200 mL of the antibody titer-increasing agent, for example an adjuvant, per day, from the viewpoint of ease of ingestion and the antibody titer-increasing effect, for example an adjuvant effect.

In one embodiment of the present invention, when the antibody titer-increasing agent, for example an adjuvant, is a solid or a semi-solid, it is preferable to ingest 10 to 1000 g, more preferably 50 to 500 g, and yet more preferably 100 to 200 g of the antibody titer-increasing agent, for example an adjuvant, per day, from the viewpoint of ease of ingestion and the antibody titer-increasing effect, for example an adjuvant effect.

In one embodiment of the present invention, when the antibody titer-increasing agent, for example an adjuvant, is a dried product, it is preferable to ingest 0.1 to 50 g, more preferably 0.5 to 10 g, and yet more preferably 1 to 5 g of the antibody titer-increasing agent, for example an adjuvant, per day, from the viewpoint of ease of ingestion and the antibody titer-increasing effect, for example an adjuvant effect.

In one embodiment of the present invention, it is possible by the antibody titer-increasing agent, for example an adjuvant, taking a configuration in which an amount appropriate for one ingestion is in one individual package to provide an antibody titer-increasing agent, for example an adjuvant, that can exhibit the effects of the present invention more precisely.

Therefore, in one embodiment of the present invention, the antibody titer-increasing agent, for example an adjuvant, may be formed as one individual package with an amount appropriate for one day of ingestion described above.

In one embodiment of the present invention, the antibody titer-increasing agent, for example an adjuvant, may contain in one individual package lactic acid bacteria containing at least $9 \times 10^7$ cfu, preferably at least $9 \times 10^8$ cfu, and more preferably at least $9 \times 10^9$ cfu, of *Lactobacillus delbrueckii* ssp. *bulgaricus* OLL1073R-1.

Alternatively, in one embodiment of the present invention, the antibody titer-increasing agent, for example an adjuvant, may contain in one individual package lactic acid bacteria containing $9 \times 10^7$ to $10^{12}$ cfu, preferably $9 \times 10^8$ to $10^{12}$ cfu, and more preferably $9 \times 10^9$ to $10^{11}$ cfu, of *Lactobacillus delbrueckii* ssp. *bulgaricus* OLL1073R-1.

In the present invention, it is preferable to continue ingestion of the antibody titer-increasing agent, for example an adjuvant, regardless of it being before or after vaccination, for at least 3 weeks, preferably at least 5 weeks, and more preferably at least 8 weeks, in order to enhance the antibody titer-increasing effect, for example an adjuvant effect.

With or without vaccination, since the antibody titer-increasing agent, for example an adjuvant, of the present invention can be ingested safely, the upper limit for the ingestion period is not particularly limited, and it can be continued permanently. From the viewpoint of a sufficiently effective antibody titer-increasing effect, for example an adjuvant effect being obtained, up to about 12 weeks may be used as a guideline.

In one embodiment of the present invention, examples include food and drink, fermented food, and a fermented drink containing *Lactobacillus delbrueckii* ssp. *bulgaricus* OLL1073R-1 or a culture thereof. Examples of the fermented food and the fermented drink include lactic acid fermented food and drink such as yoghurt, cheese, kimchi, pickles, sauerkraut, lassi, and drinking yoghurt.

In one embodiment of the present invention, the culture of *Lactobacillus delbrueckii* ssp. *bulgaricus* OLL1073R-1 is preferably fermented milk itself from the viewpoint of palatability.

In one embodiment of the present invention, from the viewpoint of production efficiency and palatability, it is preferable to select, as a culture, fermented milk obtained using *Lactobacillus delbrueckii* ssp. *bulgaricus* OLL1073R-1 and *Streptococcus thermophilus*, for example, fermented milk obtained by fermentation using *Lactobacillus delbrueckii* ssp. *bulgaricus* OLL1073R-1 and *Streptococcus thermophilus* as a starter.

In the present specification, the 'fermented milk' means one formed by fermenting milk and includes 'fermented milk', 'lactic acid bacteria drink', 'milk drink', and 'natural cheese' defined by the Ministerial Ordinance on Milk and Milk Products Concerning Compositional Standards, etc. (MMPCCS). Examples of fermented milk include 'fermented milk' defined by MMPCCS, that is, a solid (hard type), a paste (soft type), and a liquid (drink type) formed by fermenting, with lactic acid bacteria or yeast, milk such as raw milk, cow's milk, special milk, raw goat milk, sterilized goat milk, raw sheep milk, composition-modified milk, low-fat milk, fat-free milk, and processed milk, or milk containing the same level or higher of fat-free milk solids, or one obtained by freezing same.

Typical examples of fermented milk include yoghurt. The international standard defined by the U.N. Food and Agriculture Organization (FAO)/World Health Organization (WHO) also specifies that the 'product called yoghurt is made from a dairy product such as milk and skimmed milk powder by lactic acid fermentation with both *Streptococcus thermophilus* and *Lactobacillus delbrueckii* ssp. *Bulgaricus* bacteria, large amounts of the two bacteria living in the final product'. In the present specification, the 'yoghurt' referred to includes yoghurt defined by the FAO/WHO as described above.

In one embodiment of the present invention, the fermented milk is suitably fermented milk, in particular, a yoghurt such as plain yoghurt, hard yoghurt (set type yoghurt), soft yoghurt, or drinking yoghurt, produced using *Lactobacillus delbrueckii* ssp. *bulgaricus* as a starter bacterium.

In one embodiment of the present invention, from the viewpoint of production efficiency and palatability, the fermented milk is preferably fermented milk produced using *Lactobacillus delbrueckii* ssp. *bulgaricus* OLL1073R-1 and *Streptococcus thermophilus* as starter bacteria.

The present invention is explained below in further detail by reference to Examples, but the present invention is not limited to these Examples and may be modified in a variety of ways as long as the modifications do not depart from the technical scope of the present invention.

EXAMPLES

Production Example 1

Production of *Lactobacillus delbrueckii* ssp. *Bulgaricus* OLL1073R-1 Culture and Placebo

*Lactobacillus delbrueckii* ssp. *bulgaricus* OLL1073R-1 and *Streptococcus thermophilus* OLS3059 were added as a starter to mixture A containing a dairy product, sugar, and starting water and fermented at 43° C. for 4 hours, and mixture B containing glucose syrup, sugar, pectin, fragrance, stevia, and starting water was added thereto, thus producing a drink type yoghurt (hereinafter, called 'yoghurt R-1 drink type').

A sour milk drink (hereinafter, a 'placebo drink') was produced by mixing the same starting materials as for mixture A and mixture B above at the same compounding ratio, and by adding lactic acid thereto.

Capped PET bottles were filled with 112 mL of yoghurt R-1 drink type and the placebo drink.

Example 1

<Ingestion Plan>

A randomized double-blind placebo control test was carried out using as subjects 40 male university students (average age: 19.4 years old (18 to 25 years old)).

Test subjects were divided into two groups, one of the groups ingested one bottle (112 mL)/day of yoghurt R-1 drink type produced in Production Example 1 (R-1 ingestion group), and the other group ingested one bottle (112 mL)/day of placebo drink produced in Production Example 1 (placebo group). The ingestion period therefor was 8 weeks before a winter holiday and 2 weeks after the winter holiday. 3 weeks after starting the test, vaccination with an influenza vaccine (mixture of three types, A virus H1N1, A virus H3N2, and B virus) was carried out.

<Evaluation Items>

Blood was sampled on the day of starting ingestion of yoghurt R-1 drink type or placebo drink (Day 1), 1 week after influenza vaccination (Day 29), 5 weeks after influenza vaccination (Day 57), about 8 weeks after influenza vaccination (Day 76), and about 10 weeks after influenza vaccination (Day 89, day of ending ingestion of yoghurt R-1 drink type or placebo drink), and the influenza-specific antibody titer was measured by the HI method.

These schedules are shown in FIG. 6.

As a result, about 8 weeks after the influenza vaccination (mixture of three types, A virus H1N1, A virus H3N2, and B virus), in the R-1 ingestion group, compared with the placebo group, the antibody titer against influenza A virus H3N2 was a significantly high value (FIG. 1-2).

In this case, in the R-1 ingestion group, compared with the placebo group, the antibody titer against influenza A virus H1N1 was generally a low value (FIG. 1-1).

In addition, in the R-1 ingestion group, compared with the placebo group, the antibody titer against influenza B virus was a high value (FIG. 1-3).

The 'antibody titer' referred to here has the following meaning.

<Antibody Titer>

When infected with a virus, antibodies are produced in the serum, and it is an indicator showing the amount of antibodies produced against an antigen such as a virus.

For example, an influenza virus has the property of making red blood cells of an animal agglutinate. When an antibody is present in the blood, an antigen-antibody reaction occurs between the antigen of the virus and the antibody, and the ability to agglutinate red blood cells is suppressed. A method for measuring the amount of antivirus antibody in blood utilizing this property is a hemagglutination inhibition test and is used in the measurement of an 'antibody titer' for measles and rubella viruses, etc.

Specifically, the serum is diluted at a predetermined dilution ratio, and a fixed amount of virus is added thereto and reacted. A red blood cell suspension is added thereto, and the dilution ratio at which agglutination of red blood cells is suppressed is determined. The final dilution ratio at which agglutination of red blood cells is completely suppressed is defined as the HI 'antibody titer'.

On the other hand, about 5 weeks after immunization with the influenza vaccine (combined vaccine of three types, A virus H1N1, A virus H3N2, and B virus), the R-1 ingestion group showed significantly high seroconversion rates for the influenza A virus H1N1 and A virus H3N2 compared with the placebo group (FIG. 2-1 and FIG. 2-2).

Furthermore, in the R-1 ingestion group, about 8 weeks after the influenza vaccination the seroconversion rate for the influenza A virus H3N2 exceeded 40%, which is considered to be an international standard for vaccine efficacy (European Medicines Agency Standard), whereas in the placebo group it did not exceed 40% after the influenza vaccination (FIG. 2-2).

In the R-1 ingestion group, the seroconversion rate for the influenza B virus always exceeded 40% after the influenza vaccination, whereas in the placebo group it was less than 40% about 8 weeks after the influenza vaccination (FIG. 2-3).

The broken lines showing 40% in FIG. 2-1 to FIG. 2-3 denote the international standard for vaccine efficacy (European Medicines Agency Standard).

The 'seroconversion rate' referred to here has the following meaning.

<Seroconversion Rate>

This is the proportion of subjects whose HI 'antibody titer' is less than 10 before vaccination and is at least 40 after vaccination or whose HI 'antibody titer' is at least 10 before and increases by at least 4 times after vaccination.

The antibody prevalence rates of the influenza A virus H1N1 and A virus H3N2 exceeded 70% even before the influenza vaccination, which is considered to be the international standard for vaccine efficacy (European Medicines Agency Standard) for both the R-1 ingestion group and the placebo group (FIG. 3-1 and FIG. 3-2).

In the R-1 ingestion group, the antibody prevalence rate for the influenza B virus exceeded 70%, which is considered to be the standard for influenza vaccine efficacy, 1 week and about 5 weeks after the vaccination, whereas in the placebo group, it did not exceed 70% even after the influenza vaccination (FIG. 3-3).

The broken lines showing 70% in FIG. 3-1 to FIG. 3-3 denote the international standard for vaccine efficacy (European Medicines Agency Standard).

The 'antibody prevalence rate' referred to here has the following meaning.

<Antibody Prevalence Rate>

This is the proportion of people whose HI 'antibody titer' is at least 40 times.

Since the influenza A virus H3N2 and B virus are novel vaccine strains, it has been suggested that there is a possibility that ingestion of *Lactobacillus delbrueckii* ssp. *bulgaricus* OLL1073R-1 and/or a culture thereof will result in a higher antibody titer-increasing effect, for example an adjuvant effect, being exhibited toward a novel influenza vaccine.

It can be appreciated from the above results that, in a young adult such as a student having a normal high immunological function, the antibody titer is increased by ingestion of the *Lactobacillus delbrueckii* ssp. *bulgaricus* OLL1073R-1 and/or a culture thereof of the present invention.

Since the antibody titer can be increased for a young adult, it can be anticipated that the antibody titer will increase over a wide range of ages including the elderly, pregnant women, and children.

Example 2

<Animal Experiment Plan>

4-week old BALB/c female mice (Charles River Laboratories International, Inc.) were conventionally acclimatized by free-feeding with MF solid feedstuff (Oriental Yeast Co., Ltd.) and UV sterilized water for 7 days. They were divided into 8 animals and 10 animals so that the average body weight and distributions were of the same order, and up until completion of the test, Group 1 (unfermented milk ingestion group (placebo group)) was subjected to oral administration of unfermented milk (cow's milk, skimmed milk powder, sugar, sweetener) and Group 2 (yoghurt R-1 ingestion group (R-1 ingestion group)) was subjected to oral administration of yoghurt R-1 (yoghurt formed by fermenting unfermented milk by adding yoghurt R-1 starter) at 0.4 mL/body once/day using a stomach tube. After administration thereof for 3 weeks (Day 0), Group 1 (unfermented milk ingestion group) and Group 2 (yoghurt R-1 ingestion group) were both subjected to intraperitoneal administration with 10 mg/body (250 μL physiological saline solution) of ovalbumin (OVA) as a model antigen. After an interval of 1 week (Day 7), immunization was carried out again, 1 week after the second immunization (Day 14) partial blood sampling was carried out, and after 2 weeks (Day 21) exsanguination from the axillary artery was carried out under isoflurane anesthesia. The blood thus collected was subjected to centrifugation, thus preparing the plasma, and the OVA-specific antibody titer in the plasma was measured by an ELISA method. The antibody titer was compared between Group 1 (unfermented milk ingestion group) and Group 2 (yoghurt R-1 ingestion group). Statistical processing employed a t test.

Figure 7:
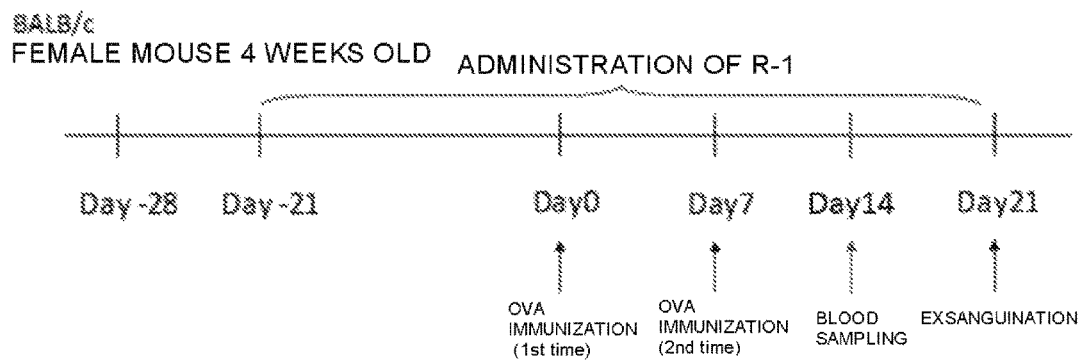
FIG. 7 A diagram showing schedules for administration of R-1, immunization, blood sampling, and exsanguination.

The schedules therefor are shown in FIG. 7.

<ELISA Measurement>

ELISA measurement employed Mouse IgG1 ELISA Quantitation Set (catalog number E90-105), Mouse IgG2a ELISA Quantitation Set (catalog number E90-107), Mouse IgG2b ELISA Quantitation Set (catalog number E90-109), and Mouse IgE ELISA Quantitation Set (catalog number E90-115), which are commercial ELISA kits from BETHYL Laboratories. Apart from the ELISA plate being first coated with OVA, this process was carried out basically in accordance with the ELISA kit protocol and the usual ELISA method. As a sample plate, F96 CERT. MAXISORP NUNC-IMMUNO PLATE (NUNC, catalog number 439454) was used. When the IgE antibody titer was measured, it was carried out in accordance with the ELISA kit protocol.

100 μg/ml of OVA dissolved in a coating buffer (0.05M Carbonate-Bicarbonate, pH 9.6) was added to a sample plate at 100 μL/well (in the case of IgE ELISA measurement alone, a coating antibody solution included with the ELISA kit was added to the sample plate at 100 μL/well). As the coating buffer, one in accordance with the instruction leaflet of the ELISA kit was prepared. The sample plate was allowed to stand at 4° C. overnight. After washing four times using a washing buffer (1×TBS, 0.05% Tween-20), a blocking solution (1% BSA, 1×TBS) was added at 200 μL/well, and it was allowed to stand at room temperature for 30 minutes. After washing four times with the washing buffer, a standard sample was added at 100 μL/well, and it was allowed to stand at room temperature for 1 hour. After washing four times with the washing buffer, a secondary antibody solution was added at 100 μL/well, and the sample plate was allowed to stand at room temperature for 1 hour. After washing four times with the washing buffer, a substrate solution (BD OptEIA® TMB Substrate Reagent Set (BD Bioscience, catalog number 555214)) was added at 100 μL/well, and it was allowed to stand at room temperature for 15 minutes while shielding it from light. A reaction stopper (0.18M $H_2SO_4$) was added at 100 μL/well, the absorbance (OD) was set at 450 nm, and each sample was subjected to measurement. The 1×TBS was prepared by diluting 10×TBS (500 mM Tris, 1.4 M NaCl, pH 8.0). A blocking solution was used for sample dilution and also for a secondary antibody solution. The results of the ELISA measurement are shown in FIGS. 4-1 to 4-3 and FIGS. 5-1 to 5-4.

<Calculation of Antibody Titer>

The antibody titer in the plasma was calculated by generating a calibration curve by serially diluting a standard plasma containing a high content of OVA-specific antibody prepared in advance. In this process, calculation was carried out by determining the IgG1 antibody titer in the standard plasma to be $10^7$ arbitrary units (AU)/ml and the IgG2a antibody titer to be $10^6$ AU/ml.

<Preparation of Standard Plasma>

Preparation of the standard plasma was carried out by the procedure below. Five 4-week old BALB/c female mice (Charles River Laboratories International, Inc.) were conventionally acclimatized by free-feeding with MF solid feedstuff (Oriental Yeast Co., Ltd.) and UV sterilized water for 7 days. After acclimatization (Day 0) 100 μg/body (250 μL complete Freund's adjuvant emulsion) of OVA was administered intraperitoneally. 2 weeks after the first immunization (Day 14), 100 μg/body (250 μL incomplete Freund's adjuvant emulsion) of OVA was administered intraperitoneally. 2 weeks after the second immunization (Day 28), exsanguination from the axillary artery was carried out under isoflurane anesthesia. The blood thus collected was subjected to centrifugation, thus preparing the plasma, and the OVA-specific IgG1 antibody titer and IgG2a antibody titer were measured by an ELISA method. From the measurement results, a plasma having a high OVA-specific antibody titer was defined as a standard plasma.

1 week (Day 14) after the OVA immunization, no significant difference in the IgG1 and IgG2b antibody titers against the OVA antigen between the placebo group and the R-1 ingestion group was observed, but there was a tendency for a high average value (FIG. 4-1 and FIG. 4-3). The IgG2a antibody titer against the OVA antigen was markedly high for the R-1 ingestion group compared with the placebo group (FIG. 4-2).

Furthermore, 2 weeks after the OVA immunization (Day 21), there was no significant difference in the IgG1 antibody titer against the OVA antigen between the placebo group and the R-1 ingestion group, but there was a tendency for a high average value of the antibody titer in the R-1 ingestion group compared with the placebo group (FIG. 5-1). The IgG2a antibody titer against the OVA antigen was markedly high for the R-1 ingestion group compared with the placebo group (FIG. 5-2), and the IgG2b antibody titer against the OVA antigen was markedly high for the R-1 ingestion group compared with the placebo group (FIG. 5-3).

Furthermore, when the antibody titer was compared between 1 week (Day 14) and 2 weeks (Day 21) after the OVA immunization, the IgG1, IgG2a, and IgG2b antibody titers were maintained at a high level in the R-1 ingestion group, and the IgG2a and IgG2b antibody titers in particular were maintained at a markedly high level in the R-1 ingestion group. This therefore shows that production of antibodies was maintained at a high level by ingestion of *Lactobacillus delbrueckii* ssp. *bulgaricus* OLL1073R-1 and/or a culture thereof.

In addition, 2 weeks after the OVA immunization (Day 21), there was no significant difference in the total IgE antibody titer between the placebo group and the R-1 ingestion group (FIG. 5-4). It is assumed from this result that the IgE antibody titer was not increased by ingestion of R-1.

The above results show that production of IgG antibodies, in particular production of IgG2a and IgG2b antibodies, was markedly induced by ingestion of *Lactobacillus delbrueckii* ssp. *bulgaricus* OLL1073R-1 and/or a culture thereof. Furthermore, production of these antibodies was maintained at a high level.

It is assumed that production of IgG2a and IgG2b antibodies having complement-activating potency and effector cell-activating potency for T cells, NK cells, neutrophils, macrophages, etc. is increased by ingestion of *Lactobacillus delbrueckii* ssp. *bulgaricus* OLL1073R-1 and/or a culture thereof, and CDC activity and ADCC activity are enhanced. It is therefore expected that ingestion of the culture will lead to general prevention of infection or prevention of advancement in severity. Moreover, since the production of various antibodies in a mouse was increased by ingestion of the culture, it is assumed that there is a possibility that the production of various antibodies will be increased in humans and that it will lead to a general prevention of infection or prevention of advancement in the severity of infection.

Generalizing the above results, *Lactobacillus delbrueckii* ssp. *bulgaricus* OLL1073R-1 and/or a culture thereof can induce an antigen-specific immunoresponse and can be expected to be a safe and simple antibody titer-increasing agent, for example an adjuvant.

The invention claimed is:

1. An adjuvant for a vaccine, comprising a package containing 100 to 200 g or 100 to 200 mL of a culture obtained by anaerobically culturing a medium containing an ingredient selected from raw milk (unpasteurized milk), pasteurized milk, full fat condensed milk, whole milk powder, skimmed milk, skimmed condensed milk, skimmed milk powder, milk protein concentrate (MPC), whey, whey powder, desalted whey, desalted whey powder, whey protein concentrate (WPC), whey protein isolate (WPI), α-lactoalbumin (α-La), β-lactoglobulin (β-Lg), casein, sodium caseinate, calcium caseinate, cream, butter, saccharides (including lactose), and a yeast extract with *Lactobacillus delbrueckii* ssp. *bulgaricus* OLL1073R-1(Deposit Accession Number: FERM BP-10741) and *Streptococcus thermophilus* at a temperature of 35° C. to 45° C. for 2 to 24 hours.

2. The adjuvant according to claim 1, wherein it is an adjuvant for a vaccine for an infectious disease.

3. The adjuvant according to claim 2, wherein the infectious disease is influenza.

4. The adjuvant according to claim 1, wherein it comprises $9 \times 10^7$ to $10^{12}$ cfu lactic acid bacteria per package.

5. A method for increasing an antibody titer, the method comprising a subject ingesting or being made to ingest the adjuvant according to claim 1.

6. The method according to claim 5, wherein ingestion of 10 to 1000 g or 10 to 1000 mL of the adjuvant per day is continued for at least three weeks.

7. The method according to claim 6, wherein ingestion of the adjuvant is continued from at least one week before the date of vaccination.

8. A method for increasing an antibody titer, the method comprising administering to a subject the adjuvant according to claim 1.

9. The method according to claim 8, wherein administration of 10 to 1000 g or 10 to 1000 mL of the adjuvant per day is continued for at least three weeks.

10. The method according to claim 9, wherein administration of the adjuvant is continued from at least one week before the date of vaccination.

11. The adjuvant according to claim 1, wherein the *Streptococcus thermophilus* is *Streptococcus thermophilus* OLS3059 (Deposit Accession Number: FERM BP-10740).

\* \* \* \* \*